US006939852B2

(12) United States Patent
Graham

(10) Patent No.: US 6,939,852 B2
(45) Date of Patent: *Sep. 6, 2005

(54) METHODS AND COMPOSITIONS FOR THE TREATMENT OF CEREBRAL PALSY

(75) Inventor: Herbert Kerr Graham, Victoria (AU)

(73) Assignee: Allergan, Inc., Irvine, CA (US)

( * ) Notice: Subject to any disclaimer, the term of this patent is extended or adjusted under 35 U.S.C. 154(b) by 434 days.

This patent is subject to a terminal disclaimer.

(21) Appl. No.: 10/104,899

(22) Filed: Mar. 22, 2002

(65) Prior Publication Data

US 2002/0102275 A1 Aug. 1, 2002

Related U.S. Application Data

(63) Continuation-in-part of application No. 08/211,352, filed as application No. PCT/GB92/01697 on Sep. 16, 1992.

(30) Foreign Application Priority Data

Sep. 24, 1991 (GB) ............................................. 9120306

(51) Int. Cl.[7] ........................ A61K 38/00; A61K 39/00; C07K 14/33
(52) U.S. Cl. ........................ 514/12; 514/21; 424/184.1; 424/236.1; 424/247.1; 530/350; 604/51
(58) Field of Search .................. 514/21, 12; 424/184.1, 424/84.1, 236.1, 247.1; 530/350; 604/51

(56) References Cited

U.S. PATENT DOCUMENTS

| | | | |
|---|---|---|---|
| 4,932,936 A | 6/1990 | Dykstra et al. | |
| 5,053,005 A | 10/1991 | Borodic | |
| 5,298,019 A | 3/1994 | Borodic | |
| 6,395,277 B1 * | 5/2002 | Graham | 424/184.1 |
| 6,448,231 B2 * | 9/2002 | Graham | 514/21 |

FOREIGN PATENT DOCUMENTS

DE          19852981       5/2000

OTHER PUBLICATIONS

Bodde H.E., et al., Transdermal Peptide Delivery, Biochem Soc Trans 17(5);943–5: 1989.
Botulinum toxin may be useful in range of muscular disorders, Int Med News 1991 Aug. 15;24(16):36 Author unknown (Abstract).
Brin, M., et al., Assessment: The clinical usefulness of botulinum toxin–A in treating neurologic disorders, Neurology 1990;40:1332–1336.
Choi, H–K, et al., Transdermal delivery of bioactive peptides: the effect of n–decylmethyl sulfoxide, pH, and inhibitors on Enkephalin metabolism and transport, Pharm Res 7(11):1099–1106 (1990).
Cioffi, G.A., et al., Microvasculature of the Anterior Optic Nerve, Survey of Opthalmology, vol. 38, Suppl., May 1994.
Consensus Conference, Clinical Use of Botulinum Toxin, Connecticut Medicine, vol. 55, No. 8, pp 471–477 (1991).
Clinical Use of Botulinum Toxin, NIH Consens Statement, 1990 Nov. 12–14; 8(8):1–20.
Cosgrove et al., Botulinum toxin A prevents the development of contractures in the hereditary spastic mouse model, Dev Med and Child Neurol. 1994, 36, 379–385.
Cosgrove et al., Botulinum toxin in the management of lower limb in cerebral palsy, Dev Med and Child Neurol. 1994, 36, 386–396.
Das, T.K., et al. Effect of treatment with botulinum toxin on spasticity, Postgraduate Medical Journal (1989) 65,208–210.
Duane, D.D., Spasmodic Torticollis, In: Jankovic J., ed., Advances in Neurology, vol. 49, Facial Dyskinesias, NY, Raven Press; 1988:pp 135–50 (Abstract).
Dunn, W.J., et al., Botulinum Toxin for the Treatment of Dysthyroid Ocular Myopathy, Ophthalmology, vol. 93, No. 4, Apr. 1986, pp. 470–475.
Hatheway, C.L., Bacterial Sources of Clostridial Neurotoxins, Chapter 1, pp. 3–24, L.L. Simpson, editor, Botulinum Neurotoxin and Tetanus Toxin, Academic Press, Inc. 1989.
Jankovic, J. et al., Therapeutic Uses of Botulinum Toxin, The New England Journal of Medicine, vol. 324, Apr. 25, 1991, No. 17, pp 1186–1194.
Liedtke, R.K., et al., Transdermal administration of insulin in type II diabetes, Results of a clinical pilot study; Arneimittelforschung 40(8); 884–6:1990 (German) (English abstract).
Overmyer, R.H., Botulinum toxin: poison with a purpose, Mod Med Sep. 1991;59:112–6 (Abstract).
Park et al., Binding of *Clostridium botulinum* type B toxin to rat brain synaptosome, Fems Microbiol Lett., 1990; 60(3):243–7. (Abstract).
Rosenbaum, A.L., et al., Vertical rectus muscle transposition and botulinum toxin (Oculinum) to medical rectus for abducens palsy, Arch Ophthalmol Jun. 1989; 107(6):820–3, (Abstract).
Sanders, L.M., Drug delivery systems and routs of administration of peptide and protein drugs, Eur J of Drug Metabolism and Pharmacokinetics, 1990, vol. 12, No. 2, pp. 95–102.
Sasaki, H. et al., Effect of pyrrolidone derivatives on lipid membrane and protein conformation as transdermal penetration enhancer, J. Pharmacobio–Dyn., 13; 468–474: 1990.
Sato et al., Purification and some properties of a proteinase and an esterase released from *Clostridium botulinum* A, B, and F types, Nippon Saikingaku Zasshi 1973; 28(4):367–74. (Abstract Only).

(Continued)

*Primary Examiner*—Jon Weber
*Assistant Examiner*—Abdel A. Mohamed
(74) *Attorney, Agent, or Firm*—Stephen Donovan

(57) ABSTRACT

The invention provides for the use of a *botulinum* toxin to treat cerebral palsy in juvenile patients by transdermal administration of the *botulinum* toxin. The juvenile patients are preferably juveniles of up to 6 years in age.

9 Claims, No Drawings

OTHER PUBLICATIONS

Schwartz, B., Circulatory Defects of the Optic Disk and Retina in Ocular Hpertension and High Pressure OpenAngle Glaucoma, Survey of Ophthalmology, vol. 38, Suppl. May 1994.

Scott, A.B., et al., Botulinum Toxin Injection in the Management of Lateral Rectus Paresis, Ophthalmology, vol. 92, No. 5, May 1985, pp. 676–683.

Snow, B.J., et al., Treatment of Spasticity with Botulinum Toxin: A Double–Blind Study, Annals of Neurology, vol. 28, No. 4, Oct. 1990, pp. 512–515.

Srinivasan, V., et al., Iontophoresis of polypeptides: effect of ethanol pretreatment of human skin, J. Pharm Sci 79(7), Jul. 1990.

Tonnesen, P., et al., A double blind trial of a 16–hour transdermal nicotine patch in smoking cessation, New Eng J Medicine, 325(5); 311–315:Aug. 1991.

Verhoef, J.C., et al., Transport of peptide and protein drugs across biological membranes, Eur J Drug Metab Pharmacokinet 1990, Apr.–Jun.;15(2):83–93.

Wright, James, et al, *The Spastic Mouse and the search for an animal model of spasticity in human beings*, Clinical Orthop. and Related Research, Apr. 1990, No. 253, pp. 12–19.

* cited by examiner

METHODS AND COMPOSITIONS FOR THE TREATMENT OF CEREBRAL PALSY

CROSS REFERENCE

This application is a continuation in part of Ser. No. 08/211,352, filed Jun. 27, 1994, which is a section 371 application from PCT/GB92/01697, filed Sep. 16, 1992, which claims priority to GB 9120306.7, filed Sep. 24, 1991.

BACKGROUND

The present invention relates to the treatment of cerebral palsy in a juvenile patient and in particular to the promotion of normal muscle growth in a juvenile patient suffering from dynamic contractures caused by cerebral palsy.

Cerebral palsy is a collective name given to a range of conditions caused by brain injury caused at or around the time of birth, or in the first year of an infant's life. The brain injury may be caused, for example, by trauma during delivery. It may also arise through such causes as trauma due to road traffic accidents or meningitis during the first year of life. It has been found that there is an increased risk of cerebral palsy in prematurely born babies and, as a result of the improvements in technology which enable premature babies to be kept alive from a much earlier age, the incidence of cerebral palsy in many countries is actually increasing rather than falling.

Although the brain injury causing cerebral palsy is a non-progressive injury, its effects may change as the sufferer grows older. The largest group of sufferers from cerebral palsy suffer from spastic cerebral palsy. Spastic cerebral palsy is characterized by dynamic contractures of the muscles which impair or inhibit completely the sufferer's ability to use his or her muscles. Moreover, muscle growth is impaired such that the longitudinal muscles become shorter relative to their associated bones as the infant grows older. Where the leg muscles are affected, the mobility of the sufferer can be severely reduced. Conventional attempts to cure this defect and to restore a measure of normal mobility typically have involved surgical intervention to alter the lengths of the tendons once the state has been reached at which the knee joint can no longer be straightened or the sufferer can only walk on tiptoe.

There remains a need for a treatment which allows the longitudinal muscles to grow normally, thereby removing, or at least minimizing the need to resort to surgical intervention. Moreover, there remains a need for a treatment which can augment surgical intervention to improve the mobility of the sufferer.

A bacterial toxin, *botulinum* toxin, has been used in the treatment of a number of conditions involving muscular spasm, for example a blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in paralysis, and hence relaxation, of the muscle afflicted by spasm.

The term Botulinum toxin is used herein as a generic term embracing the family of toxins produced by the anaerobic bacterium Clostridium *botulinum* and, to date, seven immunologically distinct toxins have been identified. These have been given the designations A, B, C, D, E, F and G. For further information concerning the properties of the various *botulinum* toxins, reference is made to the article by Jankovic & Brin, The New England Journal of Medicine, pp 1186–1194, No. 17, 1991 and to the review by Charles L. Hatheway, Chapter 1 of the book entitled "Botulinum Neurotoxin and Tetanus Toxin" Ed. L. L. Simpson, published by Academic Press Inc., of San Diego, Calif. 1989, the disclosures of which are incorporated herein by reference.

The Jankovic and Brin article reviews the use of *botulinum* toxin type A by intramuscular injection to treat focal dystonias, strabismus, blepharospasm and other facial nerve disorders, including hemifacial disorders and use with regard to other spastic conditions is also reviewed. The Hatheway publication reviews the properties of *botulinum* toxin and tetanus toxin and the organisms which produce them, noting on page 5 that subcutaneous injection of the toxin has been carried out.

The neurotoxic component of *botulinum* toxin has a molecular weight of about 150 kilodaltons and is thought to comprise a short polypeptide chain of about 50 kD which is considered to be responsible for the toxic properties of the toxin, and a larger polypeptide chain of about 100 kD which is believed to be necessary to enable the toxin to penetrate the nerve. The "short" and "long" chains are linked together by means of disulphide bridges.

The neurotoxic polypeptide component is present in a complex with non-toxic proteins and haemagglutinins, the molecular weight of the complex being in the region of 900 kD.

Botulinum toxin is obtained commercially by establishing and growing cultures of C. *botulinum* in a fermenter and the harvesting and purifying the fermented mixture in accordance with known techniques.

The "A" form of *botulinum* toxin is currently available commercially from several sources, for example, from Porton Products Ltd., UK under the tradename "DYSPORT", and from Allergan Inc., Irvine, Calif. under the trade name "OCULINUM."

DESCRIPTION

It has now been found by the present inventor that children suffering from cerebral palsy related dynamic muscle contractures exhibit improvements in function following treatment with a *botulinum* toxin and that such functional improvements persist when the tone reducing effects of the toxin have worn off.

It has also been found that by administering a *botulinum* toxin to a juvenile spastic mammal during its growth phase, the consequent reduction in tone of the spastic muscle enables increased longitudinal growth of the muscle to take place.

In a first aspect, the present invention provides a method of treating a juvenile patient suffering from arrested muscle growth arising from the presence of dynamic contractures of the muscle, which method comprises administering to the patient a therapeutically effective amount of substance which blocks the release of synaptic vesicles containing acetylcholine.

The present invention also provides a method of treating a juvenile patient suffering from cerebral palsy, which method comprises administering to the patient a therapeutically effective amount of substance which blocks the release of synaptic vesicles containing acetylcholine.

In a further aspect the invention provides a method of treating a juvenile patient suffering from arrested muscle growth arising from the presence of dynamic contractures of the muscle, which method comprises administering to the patient a therapeutically effective amount of a presynaptic neurotoxin, for example a bacterial neurotoxin such as a *botulinum* toxin.

In a still further aspect the invention provides a method of treating a juvenile patient suffering from arrested muscle growth due to a cerebral palsy, which method comprises administering a presynaptic neurotoxin (for example a bacterial neurotoxin such as a *botulinum* toxin) to the patient in a non toxic amount sufficient to reduce muscle tone and promote improved muscle growth.

The *botulinum* toxin used according to the present invention preferably is Botulinum toxin A. Botulinum toxin A is available commercially from Porton Products Limited, UK, and from Allergan Inc., Irvine, Calif.

Administration of the toxin preferably is by means of intramuscular injection directly into a spastic muscle, in the region of the neuromuscular junction, although alternative types of administration (e.g., sub-cutaneous injection) which can deliver the toxin directly to the affected muscle region may be employed where appropriate.

Such an alternative type of administration which can deliver the toxin directly to the affected muscle region includes transdermal administration of a *botulinum* toxin. Thus, transdermal administration of proteins, such as insulin, is known and various chemical transport enhancers (such as the skin lipid fluidizer Azone), and diverse methodologies, such as ionotophoresis, have been used to enhance percutaneous penetration of peptides. See e.g. (1) Bodde H. E. et al., *Transdermal peptide delivery*, Biochem Soc Trans 17(5);943–5:1989; (2) Verhoef, J. C. et al., *Transport of peptide and protein drugs across biological membranes*, Eur J. Drug Metab Pharmacokinet 1990 April–June;15(2):83–93, and; (3) Liedtke R. K. et al, *Transdermal administration of insulin in type II diabetes. Results of a clinical pilot study;* Arneimittelforschung 40(8) ;884–6:1990 (German). For example, decylmethyl sulfoxide ("DMS") is known to increase the permeation of the skin to thereby facilitate transdermal delivery of peptides. Choi, H-K. et al., *Transdermal delivery of bioactive peptides: the effect of n-decylmethyl sulfoxide, pH, and inhibitors on Enkephalin metabolism and transport,* Pharm Res 7(11): 1099–1106 (1990). Additionally, ethanol pretreatment of the skin in conjunction with iontophoresis has also been shown to permit transdermal administration of polypeptides. Srinivasan, V. et al., *Iontophoresis of polypeptides: effect of ethanol pretreatment of human skin,* J Pharm Sci 79(7), July 1990. Thus, a variety of organic solvents as well as surfactants have been used to enhance transdermal delivery of proteins. Sasaki H. et al., *Effect of pyrrolidone derivatives on lipid membrane and protein conformation as transdermal penetration enhancer,* J Pharmacobio-Dyn., 13; 468–474: 1990.

Furthermore, use of an adhesive patch for transdermal delivery of a therapeutic drug is known. See e.g. Tonnesen, P. et al., *A double blind trial of a 16-hour transdermal nicotine patch in smoking cessation,* New Eng J Medicine, 325(5); 311–315: August 1991. The present invention encompasses an adhesive patch (as a *botulinum* toxin depot) placed onto the surface of the skin of the patient, where the patch comprises a polymeric carrier which can release a therapeutically effective amount of a *botulinum* toxin onto the skin surface of the patient. Application of a *botulinum* toxin adhesive, polymeric patch can be preceded by pretreatment of the skin with ethanol wipes or dermal abrasion, and the patch can be used concurrently or in conjunction with a suitable permeation enhancement methodology such as iontophoresis.

The toxin can be presented as a sterile pyrogen-free aqueous solution or dispersion and as a sterile powder for reconstitution into a sterile solution or dispersion.

Where desired, tonicity adjusting agents such as sodium chloride, glycerol and various sugars can be added. Stabilizers such as human serum albumin may also be included. The formulation may be preserved by means of a suitable pharmaceutically acceptable preservative such as a paraben, although preferably it is unpreserved.

It is preferred that the toxin is formulated in unit dosage form, for example it can be provided as a sterile solution in a vial, or as a vial or sachet containing a lyophilised powder for reconstituting a suitable carrier such as water for injection.

In one embodiment the toxin, e.g., *botulinum* toxin A is formulated in a solution containing saline and pasteurized human serum albumin, which stabilizes the toxin. The solution is sterile filtered (0.2 micron filter), filled into individual vials and then vacuum dried to give a sterile lyophilised powder. In use, the powder can be reconstituted by the addition of sterile unpreserved normal saline (sodium chloride 0.9% for injection).

In another embodiment, the commercially available sterile *botulinum* toxin type A powder can be incorporated into the polymeric matrix of a suitable carrier using known methodologies, and formed into an adhesive patch for use in conjunction with a skin permeation enhancer such as DMS or Azone.

In order for the benefits of the invention to be realized, administration of the *botulinum* toxin should commence before the child has completed its growing period and fixed myostatic contracture has occurred. The benefits of the invention can be maximized by administering the *botulinum* toxin to the child at an early stage in its growing period, for example before the child reaches the age of six.

The dose of toxin administered to the patient will depend upon the severity of the condition, e.g., the number of muscle groups requiring treatment, the age and size of the patient and the potency of the toxin. The potency of the toxin is expressed as a multiple of the $LD_{50}$ value of the mouse, one "unit" of toxin being defined as being the equivalent amount of toxin that kills 50% of a group of mice. The definition currently used in relation to the product marketed by Porton Products Limited. According to this definition, the potency of the *botulinum* toxin A available from Porton Products Ltd. is such that one nanogram contains 40 mouse units (units).

Typically, the dose administered to the patient will be up to about 1000 units, for example, up to about 500 units, preferably in the range from about 80 to about 460 units per patient per treatment, although smaller or larger doses may be administered in appropriate circumstances. The potency of *botulinum* toxin, and its long duration of action means that doses will tend to be administered on an infrequent basis. Ultimately, however, both the quantity of toxin administered, and the frequency of its administration will be at the discretion of the physician responsible for the treatment, and will be commensurate with questions of safety and the effects produced by the toxin.

The invention will now be illustrated in greater detail by reference to the following non-limiting examples which describe the results of clinical studies (Example 1 and Case Studies 1 and 2) with *botulinum* toxin A:

EXAMPLE 1

The Use of Botulinum Toxin A in the Management Children with Cerebral Palsy

Thirty three children suffering from cerebral palsy, having a mean age of seven years and an age range of two to seventeen years, were selected for participation in a clinical study.

The criteria for inclusion in the study were the presence of dynamic contractures interfering with function, without clinical evidence of fixed myostatic contracture. Before entering the study, all children underwent clinical evaluation, physiotherapist's assessment and parental assessment. All ambulatory patients underwent gait analysis using electrogoniometers. The children entering the study were suffering from spastic tetraplegia, diplegia, hemiplegia or monoplegia.

The hamstrings and/or calf muscles of each patient were injected with a sterile solution containing the *botulinum* toxin A (obtained from Porton Products Limited, UK). Total patient doses ranged from 80 units to 460 units (one unit being equivalent to the murine $LD_{50}$). Before injecting any muscle group, careful consideration was given to the anatomy of the muscle group, the aim being to inject the area with the highest concentration of neuromuscular junctions. Before injecting the muscle, the position of the needle in the muscle was confirmed by putting the muscle through its range of motion and observing the resultant motion of the needle end. General anesthesia, local anesthesia and sedation were used according to the age of the patient, the number of sites to be injected and the particular needs of the patient.

Following injection, it was noted that the onset of effects was complete within thirty-six to seventy-two hours and lasted from six to eighteen weeks. There were no systemic or local side-effects. All but one patient had some reduction in muscle tone; the one failure occurred early in the study and was probably the result of the toxin dosage administered (75 units) being sub-therapeutic. None of the patients developed extensive local hypotonicity. The majority of children had an improvement in function both subjectively and when measured objectively with gait analysis.

Following injection of the calf muscle groups, an assessment was made of the passive dorsiflexion at the ankle. It was found that the younger children displayed a marked improvement in passive dorsiflexion, but that for children over six years there was little improvement. This was probably due to the dynamic contracture being replaced by a fixed contracture which was unresponsive to any amount of paresis.

Case Study 1

A five year old girl with moderate right hemiplegia underwent gait analysis and, on examination, was found to have dynamic contractures of her calf and hamstrings. Gait analysis recordings of sagittal plan movements (with 95% confidence limits) were made prior to injection and these revealed that throughout the gait cycle, the knee was in excessive flexion. Gait analysis also indicated that she was in equinus throughout the gait cycle.

Following injection, the knee could be extended nearly to neutral during stance and the gait analysis pattern, although still abnormal was much improved. The ankle traces recorded indicated that she was able to dorsiflex her ankle in gait and had developed a normal range of movements.

Gait analysis was also undertaken at four months. At this stage the effects of the toxin has clinically worn off and it was found that the knee flexed to the same extent in swing that it did prior to injection. However, the gain of extension in stance was largely preserved. At the ankle, there was some relapse but there was still a lesser degree of equinus.

Case Study 2

Measurements were made of the maximal extension of the knee in a group of patients who underwent hamstring injection. Prior to injection, they all had some degree of dynamic knee flexion contracture. Four weeks following injection, this showed a highly significant improvement. However, the one patient who was least affected developed recurvatum at the knee following injection. After this, all patients who had a dynamic knee flexion contracture of less than fifteen degrees were excluded from hamstring injection. Only one local side-effect from the treatment was noted and this was a small subcutaneous haematoma which resolved itself in a few days.

EXAMPLE 2

The Treatment of the Hereditary Spastic Mouse with Botulinum Toxin A

In cerebral palsy there is frequently a failure of muscle growth leading to fixed muscular contracture. This failure has also been demonstrated in the hereditary spastic mouse (Wright J and Rang M The Spastic Mouse and the search for an animal model of spasticity in human beings) Clin. Orthop. 1990, 253, 12–19.

A study has been carried out to ascertain the effect of Botulinum Toxin A on the growth of longitudinal muscle in the spastic mouse compared with normal siblings. Groups of spastic mice at six days old had one calf muscle injected with either 1.2 units of Botulinum Toxin A or normal saline.

The mice were sacrificed at maturity and the hind limbs dissected to allow measurement of the muscle and bones.

In the control group, the spastic mice had a 13% failure of longitudinal muscle growth compared with their normal siblings. However, the muscles of the spastic mice injected with Botulinum had growth identical to that of their normal siblings. There was no difference in growth between normal mice injected with saline or Botulinum.

It can be concluded that the injection of intramuscular Botulinum toxin during the growth period of the hereditary spastic mouse allows normal longitudinal muscle growth to take place and it is believed that this finding may have significance in the management of cerebral palsy.

EXAMPLE 3

Transdermal Administration of a Botulinum Toxin

A five year old boy with moderate right hemiplegia can undergo gait analysis and, on examination, be found to have dynamic contractures of his calf and hamstrings. Gait analysis recordings of sagittal plan movements (with 95% confidence limits) can be made prior to patch application and can reveal that throughout the gait cycle, the knee is in excessive flexion. Gait analysis can also indicate that he is in equinus throughout the gait cycle.

Following ethanol pretreatment of the skin, an adhesive patch containing DMS admixed with *botulinum* toxin type A can be applied to the skin above the afflicted muscle region. Within one to two weeks subsequent to patch application, the knee can be extended nearly to neutral during stance and the gait analysis pattern, although still abnormal is much improved. Ankle trace records can indicate that he is able to dorsiflex his ankle in gait and has developed a normal range of movements.

Gait analysis can also be undertaken at four months. At this stage the effects of the toxin are expected to have clinically worn off and it can be found that the knee flexes to the same extent in swing that it did prior to application of the toxin patch. However, the gain of extension in stance can be largely preserved. At the ankle, there can be some relapse but there can still be a lesser degree of equinus. This example shows that transdermal administration of a *botulinum* toxin can be used to successfully treat juvenile cerebral palsy.

The invention has been illustrated by reference to Botulinum toxin A but it should be understood that the invention is not limited to the use of this toxin. For example, other *botulinum* toxins may be employed. Moreover, other presynaptic neurotoxins (e.g., of bacterial origin) which act in a manner similar to *botulinum* toxin may also be used. Also, synthetic analogues of the *botulinum* toxins may be envisaged wherein the 50 kD chain and/or the 100 kD chain are subjected to amino acid insertions, deletions and/or substitutions and, provided that such analogues retain the general type of activity exhibited by Botulinum toxin A, their use in the manner described hereinbefore is embraced by the present invention. The invention is also considered to embrace the use of substances structurally dissimilar to Botulinum toxin A, provided that such substances possess a prolonged ability to inhibit or block release of the synaptic vesicles containing acetylcholine.

I claim:

1. A method for treating juvenile cerebral palsy, the method comprising the step of transdermal administration of a *botulinum* toxin type A to a juvenile cerebral palsy patient, thereby treating juvenile cerebral palsy.

2. The method of claim 1 wherein the *botulinum* toxin type A is transdermally administered into a spastic muscle of the patient.

3. The method of claim 1 wherein the *botulinum* toxin type A is transdermally administered into a calf muscle or hamstring of the patient.

4. The method of claim 1, wherein the transdermal administration step is carried out by contacting a skin surface of the patient with a *botulinum* toxin depot which can release the *botulinum* toxin type A for absorption through the skin of the patient.

5. The method of claim 4, wherein the *botulinum* toxin depot is an adhesive patch which comprises a polymeric carrier for the *botulinum* toxin type A.

6. A method of treating juvenile cerebral palsy, the method comprising the step of transdermal administration of a therapeutically effective amount of a *botulinum* toxin type A to a juvenile cerebral palsy patient by contacting a skin surface of the patient with a *botulinum* toxin type A depot comprising a polymeric carrier which carrier can release the *botulinum* toxin type A for absorption through the skin surface of the patient, thereby treating juvenile cerebral palsy.

7. The method of claim 6, further comprising the step of pretreatment of the skin with a skin permeation enhancer prior to contacting the skin surface of the patient with the *botulinum* toxin type A depot.

8. The method of claim 7, further comprising the step of iontophoresis of the skin after the pretreatment step to thereby further enhance transdermal delivery of the *botulinum* toxin.

9. A method of treating a juvenile cerebral palsy, the method comprising the steps of:

(a) pretreatment of a skin surface of a juvenile cerebral palsy patient with a skin permeation enhancer;

(b) transdermal administration of a therapeutically effective amount of a *botulinum* toxin type A to a juvenile cerebral palsy patient by contacting the skin surface of the patient with a *botulinum* toxin type A depot comprising a polymeric carrier which carrier can release the *botulinum* toxin type A for absorption through the skin surface of the patient, and;

(c) iontophoresis of the skin to further enhance transdermal delivery of the *botulinum* toxin, thereby treating juvenile cerebral palsy.

\* \* \* \* \*